United States Patent [19]

O'Brien et al.

[11] Patent Number: 5,064,617

[45] Date of Patent: Nov. 12, 1991

[54] COMBUSTION SYSTEM

[75] Inventors: Larry S. O'Brien, St. Joseph; Robert G. Warren, Stevensville; Keith J. Adani, Bridgman, all of Mich.

[73] Assignee: Leco Corporation, St. Joseph, Mich.

[21] Appl. No.: 480,777

[22] Filed: Feb. 16, 1990

[51] Int. Cl.$^5$ .......................................... G01N 31/12
[52] U.S. Cl. ..................................... 422/78; 422/102; 356/312; 432/198; 432/200
[58] Field of Search ................. 422/78, 102; 356/312; 432/198, 200

[56] References Cited

U.S. PATENT DOCUMENTS

| | | | |
|---|---|---|---|
| 1,931,895 | 1/1933 | Grote et al. | 422/78 |
| 2,370,293 | 6/1943 | Dietert | 422/78 |
| 2,888,332 | 5/1959 | Aites | 422/78 |
| 3,374,064 | 5/1963 | Kolsto | 422/78 |
| 3,923,464 | 12/1975 | Sitek et al. | 23/253 |
| 3,985,505 | 10/1976 | Bredeweg | 23/230 |
| 4,244,917 | 1/1981 | Woods et al. | 422/78 |
| 4,282,183 | 8/1981 | Bredeweg et al. | 422/78 |
| 4,352,781 | 10/1982 | O'Brien | 422/78 |

FOREIGN PATENT DOCUMENTS 890191  3/1980  United Kingdom ............... 422/78

Primary Examiner—David L. Lacey
Assistant Examiner—Abanti B. Singla
Attorney, Agent, or Firm—Price, Heneveld, Cooper, DeWitt & Litton

[57] ABSTRACT

A combustion chamber includes an inner cylindrical member concentrically mounted within an outer cylindrical member with a cylindrical space therebetween. The outer cylindrical member is enclosed at one end and both cylindrical members are open at an opposite end for access to the combustion area. The by-products of combustion are withdrawn from the inner cylindrical member at the closed end of the outer cylindrical member such that they reverse direction and circulate through the hot zone of the furnace in the cylindrical space. In a preferred embodiment of the invention, a porous ceramic plug which supports and spaces the tubes in concentric relationship at the one end and captures particulate by-products of the combustion holding them in the hot zone for complete combustion.

18 Claims, 3 Drawing Sheets

COMBUSTION SYSTEM

BACKGROUND OF THE INVENTION

The present invention relates to a combustion system and particularly to an improved system for fusing a solid or liquid specimen into a gaseous sample for subsequent analysis.

There exists a variety of combustion systems for the combustion of analytical samples to determine, for example, the sulphur content of coal, coke or other substances. The sulphur level can be determined from a solid or liquid specimen which is positioned in an induction furnace and combusted to provide a gaseous sample. The gaseous sample is subsequently drawn from the combustion chamber and analyzed by an infrared or other detector for detecting the sulphur dioxide concentration which is then displayed by a digital display as the sulphur content of the specimen. Certain aspects of previous combustion systems used in such analyzers is disclosed in U.S. Pat. No. 3,923,464 issued 12/2/75 to Sitek et al and assigned to the present assignee.

Such systems are open ended and employ a carrier gas introduced into the combustion chamber of the induction furnace to oxidize the specimen and carry the resultant gas through the opposite end of the combustion chamber and to an infrared cell for detection. A closed loop combustion system of this general type is also described in U.S. Pat. No. 3,985,505 issued 10/12/76 to R.L. Bredeweg, and assigned to the present assignee.

Although these systems provide excellent results in analyzing certain specimens, coal cannot be heated directly with radio frequency energy used in these systems since it is a non-conductor. As a result, accelerating agents, such as iron chips or powder, or tungsten, are required to be added to the sample. Further, the combustion chamber in such systems is relatively small and due to the fact that the coal is naturally combustible and creates an exothermic reaction during its combustion, it tends to sputter and some of the specimen can easily escape from the hot zone of the combustion chamber and not be broken down to provide an accurate analysis.

U.S. Pat. No. 4,282,183 issued 8/4/81 to R.L. Bredeweg et al and assigned to the present assignee and U.S. Pat. No. 4,352,781 issued 10/5/82 to O'Brien and also assigned to the present assignee, disclose improved combustion chambers having relatively large hot zones and an open end for receiving a combustion boat containing the specimen to be analyzed and an enclosed opposite end. The specimen gas is withdrawn from near the closed end of the combustion chamber by an eduction tube extending within the combustion chamber. The open end of the chamber is effectively sealed by a gas curtain such that the interior of the chamber is available to the operator for readily inserting and removing specimens for combustion. The combustion system represented by these patents, provide improved results, however, they utilize a significant number of ceramic and quartz parts which must be carefully aligned and attached to one another to maintain their interrelationship for most effective operation. Thus several of the parts are cemented using a refractory cement which can break during use due in part to thermal expansion and contraction. Also, in these combustion systems, the gases pass relatively quickly through the combustion zone and are withdrawn either externally to the combustion chamber or through an eduction tube having a relatively small diameter within the combustion chamber. As a result, if the size of the combustion is too large, incomplete combustion may result in inaccurate measured specimen concentration.

SUMMARY OF THE PRESENT INVENTION

The system of the present invention, overcomes the difficulties encountered by the prior art by providing a combustion chamber defined by an inner cylindrical member concentrically mounted within an outer cylindrical member defining a cylindrical space therebetween. The outer cylindrical member is enclosed at one end and both cylindrical members are open at an opposite end for access to the combustion area. Means are provided for supporting the open cylindrical ends of the inner cylindrical member with respect to the outer cylindrical member at both ends and the by-products of combustion are withdrawn from the inner cylindrical member at the closed end of the outer cylindrical member such that they reverse direction and circulate through the hot zone of the furnace in the cylindrical space. The cylindrical space provides a relatively large volume and therefore reduces the gas flow rate allowing the combustion materials to remain in the hot zone a sufficient time for complete conversion to $SO_2$ or $CO_2$. In a preferred embodiment of the invention, the inner cylindrical member is a tube supported at the closed end of an outer cylindrical tube by means of a porous ceramic plug which supports and spaces the tubes in concentric relationship at such end and captures particulate by-products of the combustion holding them in the hot zone a sufficient time to be fully combusted. The opposite end of the concentric tubes are supported by mechanical means including seals such that cementing of the combustion chamber components is avoided. Thus an improved combustion system is provided which is relatively inexpensive and is easy to assembly and resists breakage during use and therefore has a longer life.

These and other features, objects and advantages of the present invention, will become apparent upon reading the following description thereof together with reference to the accompanying drawings in which:

DETAILED DESCRIPTION OF THE PREFERRED EMBODIMENT

Figure 1:
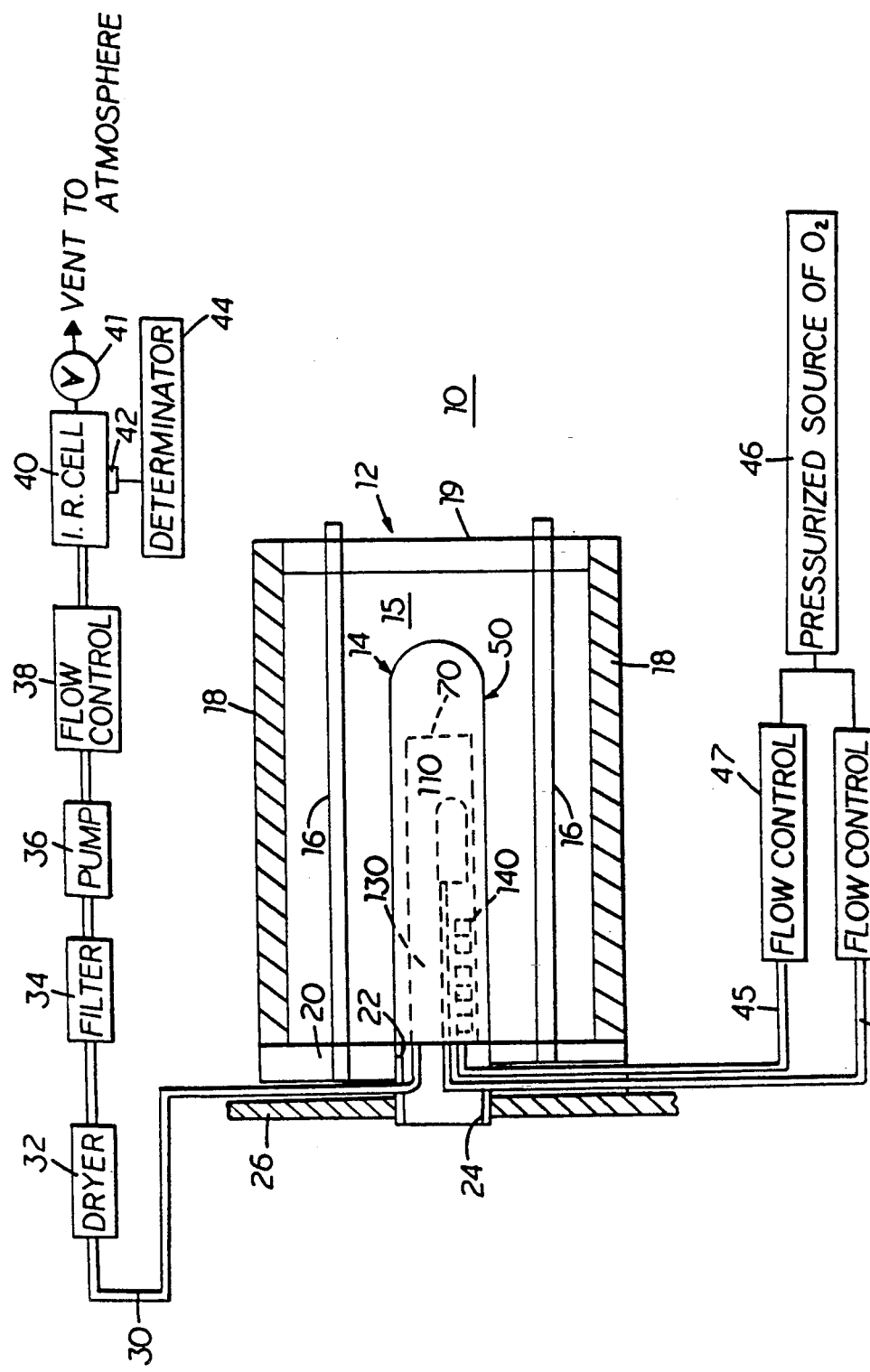
FIG. 1 is an analyzer incorporated in the combustion system of the present invention shown partly in schematic and block diagram form.

Referring initially to FIG. 1 there is shown an analyzer 10 which in the preferred embodiment, is employed for determining the percentage of sulphur content in coal and coke. Although the preferred embodiment is used with these solid materials which are pulverized into powered form for combustion, it is to be understood that the combustion apparatus of the present invention can be used with other solid or liquid materials and for determining other constituents elements of a given specimen.

The analyzer 10 comprises a combustion furnace 12 shown in top plan view partly broken away in FIG. 1 and including a combustion chamber 14 positioned within the furnace. Furnace 12 is a resistance-type furnace having three rod-shaped resistance heating elements 16 which are positioned concentrically around combustion chamber 14. The heating elements and combustion chamber are housed within a refractory container including a tubular sidewall 18, a rear wall 19, and a front wall 20 having a access opening 22 for the extension of one end of the combustion chamber through an access port 24 in the instruments front panel 26. The chamber extends slightly through and is supported at one end by wall 19 as seen in FIG. 1. Thus the combustion chamber 14 is totally enclosed within the resistance furnace. The resistant heating elements 16 are preferably silicon carbide-type resistance elements and provide heating temperatures to the interior of the combustion chamber 14 in excess of 1000° C. with a nominal operating temperature for analysis of 1,350° C. and a maximum temperature in the neighborhood of 1,500° C. Gases from the specimen being combusted within the combustion chamber are withdrawn by an eduction tube 30 which as described below is in communication with a cylindrical elongated eduction chamber of the combustion system and is coupled at one end within an exit fitting of the combustion chamber. The eduction tube 30 is coupled to an anhydrous dryer 32 for removing water from the specimen gas. It subsequently travels through a filter 34 and a pump 36 which withdraws the specimen gas from the combustion chamber. The output of pump 36 is coupled to a flow control 38 for providing a flow rate of approximately 3 liters per minute to the input of an IR cell 40. The output of the IR cell 40 is vented to the atmosphere through a barometric pressure correction valve 41 to provide a constant back pressure for the gas flow path.

IR cell 40 includes a detector 42 which is electrically coupled to a determinator 44 including electrical circuits for processing the electrical signals from detector 42 and providing a digital readout of the percentage of sulphur content in the specimen being combusted. The determinator 44, elements 32-44 are of a construction which can be the type commercially used in a Leco SC-32 sulphur determinator. Modifications to the specific electrical circuitry can be made to accommodate the system for the particular specimen gas being analyzed. In the preferred embodiment, the IR cell includes a filter for the detection of sulphur dioxide which is a combination of the element sulphur and the oxidizing gas, oxygen, which is employed in the system of the preferred embodiment.

Figure 3:
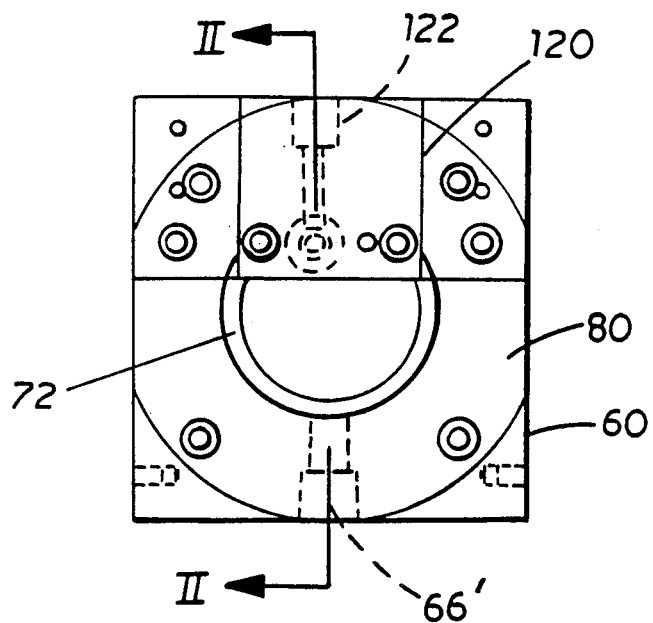
FIG. 3 is a left end elevational view of the combustion system of the present invention.
Figure 4:
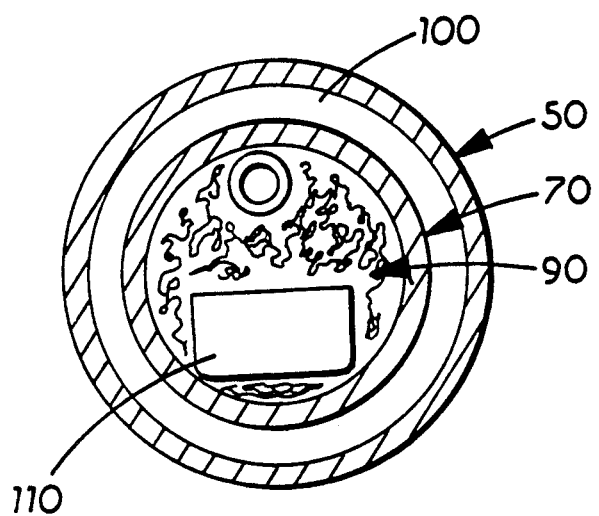
FIG. 4 is a cross-sectional view of the combustion system shown in FIG. 2 taken along section lines IV—IV of FIG. 2.

The analyzer further includes a pressurized source 46 of oxygen gas coupled to a pair of rotometers 47 and 48 which supply the oxidizing gas to the combustion chamber 14 by supply conduits 45 and 49 respectively. Thus the specimen material is combusted by the furnace 12 in the presence of oxygen to convert the sulphur contained within the specimen to sulphur dioxide and carbon to carbon dioxide for subsequent analysis. The combustion system of the present invention provides substantially complete combustion of the specimen for subsequent analysis by the determinator 44. Having briefly described the overall environment of the combustion system of the present invention, a detailed description of the combustion chamber 14 and associated improvements is now presented in conjunction with FIGS. 2-4.

Figure 2:
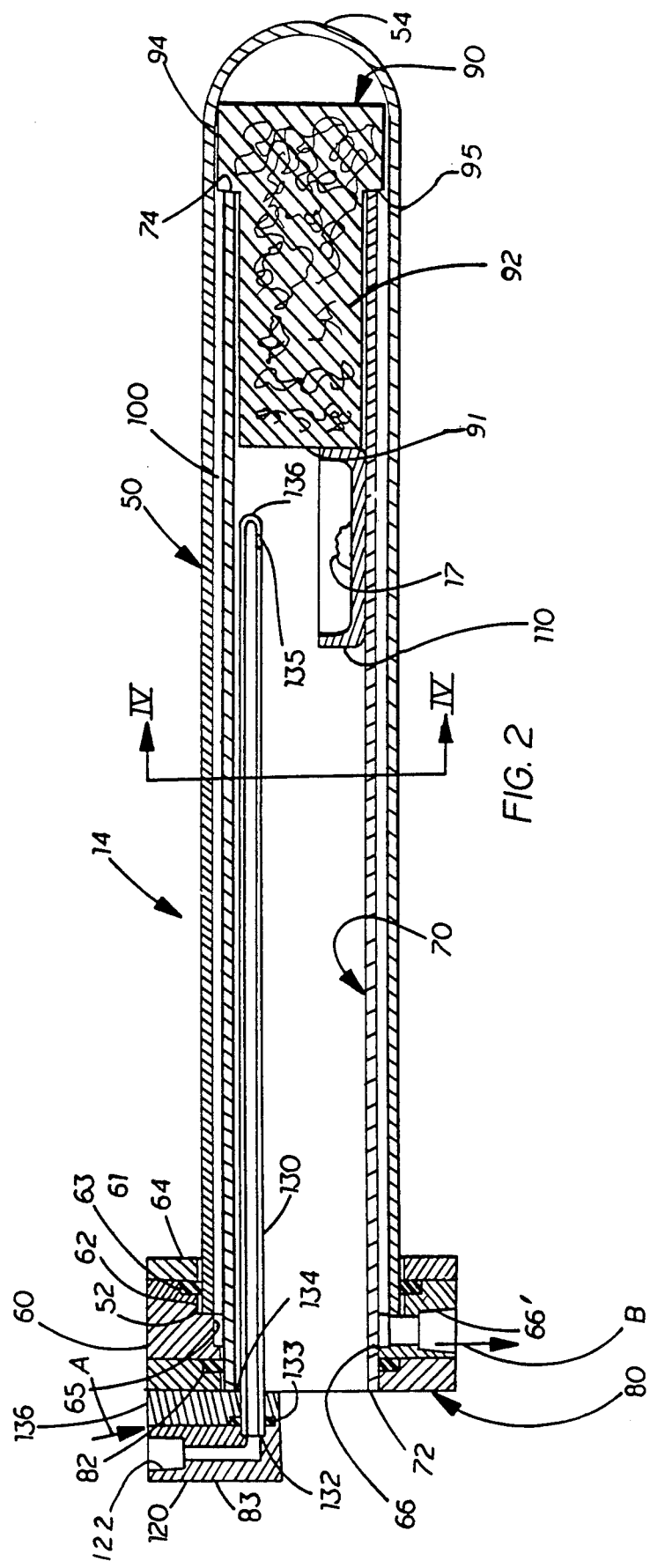
FIG. 2 is an enlarged vertical cross-sectional view of the combustion system of the present invention.

Referring initially to FIG. 2, there is shown the combustion system 14 of the preferred embodiment which includes an outer cylindrical combustion tube 50 made of mullite and having an open cylindrical end 52 and an enclosed opposite end 54 which is rounded as seen in FIG. 2. Tube 50 has an overall length of 14.62 inches and an outer diameter of 2.25 inches and an inner diameter of 2 inches. It is supported at open end 52 by a generally rectangular mounting block 60 made of stainless steel and having a first circular aperture 62 formed therein for loosely receiving end 52 which is subsequently sealed in place by a resilient silicon O-ring seal 61 mounted within a forwardly facing annular groove 63 in block 60. Ring 61 is compressively held in place by an annular compression ring 64 bolted to the forward facing side of block 60 by suitable fastening means such as bolts or the like. Block 60 also includes an smaller diameter annular recess 65 which communicates with a threaded outlet port 66' to which eduction tube 30 is mounted for withdrawing combustion gases from the combustion system 14 as described in greater detail below.

Concentrically mounted within outer combustion tube 50 is an inner combustion tube 70 also made of mullite and having an overall length of approximately 13.62 inches, an outer diameter of 1.75 inches and an inner diameter of 1.5 inches. Inner tube 70 is open at a first end 72 and at its opposite end 74 with end 72 mounted through aperture 66 in block 60 formed therein concentrically with apertures 65 and 62 and is sealed to a front mounting plate 80 by means of a resilient silicon O-ring 82 fitted within a annular groove 83 formed in front plate 80 for securing the tube in concentric spaced relationship with respect to tube 50 at first end 72.

The opposite end 74 of the open cylindrical mullite tube 70 is held in concentric spaced relationship with respect to end 54 of tube 50 by means of a porous plug 90 having an overall length of 3.88 inches and a section 92 having an outer diameter of 1.34 inches which extends within the end of end 74 of tube 70 a distance of approximately 2.88 inches. Plug 90 has an enlarged cylindrical end 94 with a should 95 which rests against end 74 of tube 70. The diameter of end 94 is approximately 1.82 inches to slide within tube 50 and hold the end 74 of tube 70 in concentric spaced relationship to tube 50.

The porous ceramic plug 90 is made of a reticulated alumina or zirconia material having a porosity of approximately 10 porous per inch. This material is commercially available from several sources including Hi-Tech Ceramics, Inc. The material allows by-products of combustion to flow therethrough and enter the cylindrical space 100 defined as the volume between the outer diameter of tube 70 and the inner diameter of tube 50. The cross-sectional annular area of space 100 is approximately 0.74 square inches which is significantly larger than that provided by the prior art eduction tubes and therefore provides a slower velocity for combustion gases to recirculate through the hot zone of the combustion chamber in which a combustion boat 110 is centered.

The combustion system 14 further includes an end fitting 120 (FIG. 2) having a threaded inlet port 122 communicating with an end 132 of a lance tube 130 sealably mounted to member 120 by means of a resilient silicon O-ring 133 mounted within an annular recess 134 of a lance mounting block 136. Blocks 120, 136 and 80 are secured to the primary mounting block 60 by means of suitable fastening bolts shown in detail in FIG. 3. Lance tube 130 is made of alumina and has a length of approximately 10.45 inches and inner diameter of 0.12 inches with an aperture 135 at an otherwise enclosed end 136 opposite end 132. Aperture 135 is centered above the combustion boat 110 to provide a flow of oxygen into the combustion boat to supply an oxidizing carrier gas for the system. A purge tube 140 (shown schematically in FIG. 1) is mounted to the open end 72 of the combustion tube 70 and receives oxygen from input line 45 as seen in FIG. 1 to effectively seal the open end of the combustion tube during an analysis. This construction is disclosed in detail in U.S. Pat. No. 4,282,183, the disclosure which is incorporated herein by reference.

In operation, a sample such as a piece of coal or coke 17 (FIG. 2) is positioned in the combustion boat 110 which is slid through the open end 72 of the combustion chamber 14 by means of a suitable push rod until it comes into contact with the end 91 of porous plug 90 thereby positioning it in the center of the combustion hot zone under lance 130. The furnace 12 is actuated to combust the specimen during which the carrier gas is inputed as indicated by arrow A in FIG. 2 to the lance and to the purge tube 140 shown in FIG. 1 for effectively sealably enclosing the open end of the combustion system. The flow rate through the lance and purge tube combined is approximately $3\frac{1}{4}$ liters-per-minute and when the furnace is heated to the operational temperature of approximately 1350° C. the specimen is combusted. Some small particulate material which may be splattered from the combustion boat will engage the porous plug 90 and be held within the edge of the combustion zone until the particulate material is fully combusted.

The gaseous by-products of combustion are drawn through the cylindrical eduction chamber 100 surrounding the outer diameter of combustion tube 70 by means of the pump 36 (FIG. 1) withdrawing the gaseous sample from the combustion system as indicated by arrow B. As the combustion gases flow through the plug 90 they reverse direction around the end 74 of tube 70 thereby mixing and homogenizing the gases as they are then re-circulated around end 72 of the cylindrical combustion tube 70 they are circulated through the hot zone of the furnace to assure the gas is fully converted to $SO_2$ or $CO_2$ and at relatively low velocity thereby assuring the time within the hot zone is increased due to the cross-sectional area of the eduction path for by-products of combustion. The lance tube is of sufficiently small size so as to be adequately supported in a cantilevered fashion as shown in FIG. 2 with the mounting block 60 and its components, the combustion system of the present invention does not require cementing the parts together nor precise positioning inasmuch as the mounting system precisely positions and seals the ends 52 and 72 of the combustion tubes while porous plug 90 positions the opposite ends of the combustion tubes in aligned spaced concentric relationship.

Thus, with the system of the present invention, a relatively inexpensive and easily disconnectable combustion system is provided which also provides improved combustion analysis due to the design of the gas flow path provided. It will become apparent to those skilled in the art that various modifications to the preferred embodiment of the invention as described herein can be made without departing from the spirit or scope of the invention as defined by the appended claims.

The embodiments of the invention in which an exclusive property or privilege is claimed are defined as follows:

1. A combustion chamber for combusting a liquid or solid specimen to a gaseous state for subsequent analysis to determine the amount of one or more constituent elements contained in the specimen comprising:
   a first generally cylindrical elongated combustion tube having a first open end and a second enclosed end and an inner diameter;
   a second generally cylindrical combustion tube having first and second open ends, said second tube having an outer diameter less than the inner diameter of said first tube;
   means for supporting said first end of said second tube in spaced generally concentric relationship with said first end of said first combustion tube; and
   rigid porous plug means coupled to said second end of said second tube so as to mount said second end of said second tube in spaced generally concentric relationship with said second end of said first tube thereby defining a generally cylindrical space between the outer diameter of said first tube and the inner diameter of said second tube so as to cause the flow of gaseous by-products of combustion from a sample positioned within said first tube to exit said apparatus for analysis.

2. The apparatus as defined in claim 1 and further including an eduction tube communicating with said cylindrical space in flow communication with said first ends of said first and second tubes so as to draw gaseous by-products of combustion through said second end of said second tube, said porous plug means and in a direction through said generally cylindrical space toward said first end of said first and second tubes.

3. The apparatus as defined in claim 2 wherein said means for supporting said first ends of said tubes comprises mounting block means having aperture means therethrough receiving said first ends of said tubes.

4. The apparatus as defined in claim 3 wherein said supporting means further includes resilient seal means so as to provide a seal between said first ends of said tubes and said mounting block means.

5. The apparatus as defined in claim 4 wherein said mounting block means includes aperture means communicating with said cylindrical space.

6. The apparatus as defined in claim 5 wherein said second tube is shorter than said first tube.

7. The apparatus as defined in claim 6 wherein said porous plug means is a ceramic plug.

8. The apparatus as defined in claim 7 wherein said ceramic plug is a reticulated ceramic plug.

9. The apparatus as defined in claim 8 and in combination with a resistance furnace and means for mounting said first and second tubes in said resistance furnace.

10. A furnace for an analytical instrument, said furnace including a combustion chamber for combusting a liquid or solid specimen to a gaseous state for subsequent analysis to determine the amount of one or more constituent elements contained in the specimen comprising:
    a first generally cylindrical elongated combustion tube having a first open end and second enclosed end and an inner diameter;

a second generally cylindrical combustion tube having first and second open ends, said second tube having an outer diameter less than the inner diameter of said first tube;

means for supporting said first end of said second tube in spaced generally concentric relationship with said first end of said first combustion tube;

means for mounting said second end of said second tube in spaced generally concentric relationship with said second end of said first tube to define a generally cylindrical space between the outer diameter of said first tube and the inner diameter of said second tube; and means for withdrawing said gaseous by-products of combustion from an end of said generally cylindrical space near said first end of said tubes such that the direction of said gaseous by-products reverse as they travel from said second tube into said generally cylindrical space.

11. The apparatus as defined in claim 10 wherein said second tube is shorter than said first tube.

12. The apparatus as defined in claim 10 wherein said means for mounting said second end of said tubes is a porous plug.

13. The apparatus as defined in claim 12 wherein said porous plug is a reticulated ceramic material.

14. The apparatus as defined in claim 13 wherein said withdrawing means includes an eduction tube coupled to said combustion chamber to communicate with said cylindrical space.

15. The apparatus as defined in claim 14 wherein said means for supporting said first ends of said tubes comprises mounting block means having aperture means therethrough receiving said first ends of said tubes.

16. The apparatus as defined in claim 15 wherein said supporting means further includes resilient seal means for sealably coupling said first ends of said tubes to said mounting block means.

17. The apparatus as defined in claim 15 wherein said mounting block means includes a plurality of sections with one section including an aperture communicating with said cylindrical space.

18. The apparatus as defined in claim 10, wherein said furnace is constructed so as to define a resistance furnace into which said first and second tubes are mounted.

* * * * *